United States Patent [19]

Feyereisen et al.

[11] Patent Number: 5,039,792
[45] Date of Patent: Aug. 13, 1991

[54] ALLATOSTATINS WHICH INHIBIT INSECT JUVENILE HORMONE BIOSYNTHESIS

[75] Inventors: René Feyereisen; Grahame E. Pratt; Dan E. Farnsworth, all of Corvallis, Oreg.; Ned R. Siegel, Belleville, Ill.; Kam F. Fok, St. Louis, Mo.

[73] Assignees: Oregon State University, Corvallis, Oreg.; Monsanto Company, St. Louis, Mo.

[21] Appl. No.: 452,163

[22] Filed: Dec. 18, 1989

[51] Int. Cl.$^5$ .......................... C07K 7/06; C07K 7/08
[52] U.S. Cl. .................................. 530/326; 530/328; 530/858
[58] Field of Search ...................... 514/13, 15, 16; 530/858, 326, 328

[56] References Cited

PUBLICATIONS

Rankin, S. M. et al., *J. Insect Physiol.*, 32:151–156, (1986).
Granger, N. A. et al., *Molecular and Cellular Endocrinology*, 49:237–248, (1987).
Rankin, S. M. et al., *J. Insect Physiol.*, 33:551–558, (1987).
Paulson, C. R. et al., *Insect Biochem.*, 17:961–964, (1987).
Menn, J. J. et al., *J. Agric. Food Chem.*, 37:271–278, (1989).
Rüegg, R. P. *Experientia*, 39:1329–1334, (1983).
Kataoka, H. et al., *Science*, 243:1481–1483, (1989).
Feyereisen, R. et al., *FEBS Letters*, 222:345–348, (1987).
Feyereisen, R. et al., *Insect Biochem.*, 17:939–942, (1987).
Meller, V. H. et al., *Molecular and Cellular Endocrinology*, 43:155–163, (1985).
Quistad, G. B. et al., *J. Agric. Food Chem.*, 33:47–50, (1985).
Kuwano, E. et al., *Agric. Biol. Chem.*, 48:3115–3119, (1984).
Edwards, J. P. et al., *J. Insect Physiol.*, 29:83–89, (1983).
Ferenz, H.-J. et al., *Z. Naturforsch*, 38c:856–858, (1983).
Woodhead, A. P. et al., *Proc. Natl. Acad. Sci. U.S.A.*, 86:5997, (1989).
Pratt, G. E. et al., *Biochem. and Biophys. Res. Comm.*, 163:1243, (1989).

*Primary Examiner*—Jeffrey E. Russel
*Assistant Examiner*—Stephen Walsh

[57] ABSTRACT

An eighteen amino acid neuropeptide isolated from brain complexes of adult female cockroach, *Diploptera punctata*, is identified as an allatostatin because it inhibits the biosynthesis of juvenile growth hormone in cockroach corpora allata. Primary structure of the isolated allatostatin is Al a-Tyr-Ser-Tyr-Val-Ser-Glu-Tyr-Lys-Arg-Leu-Pro-Val-Tyr-Asn-Phe-Gly-Leu-NH$_2$. A synthetic peptide of this sequence and three synthetic peptides with truncated sequences conserving the amidated carboxyl portion of the native sequence have allatostatin activity. Certain derivatives of the peptides also have allatostatin activity including compounds having the sequence: X-Val-Tyr-Asn-Phe-Gly-Leu-NH$_2$, in which X is Leu-Arg, Leu-Pro, Arg-Leu-Pro-, Ala-Tyr-Ser-Tyr-Val-Ser-Glu-Tyr-Lys-Arg-Leu-Pro, acetyl-Ala-Tyr-Ser-Tyr-Val-Ser-Glu-Tyr-Lys-Arg-Leu-Pro, or acetyl-Arg-Leu-Pro. These peptides have the potential for regulating the growth of certain insects, and may be useful in the area of insect control.

7 Claims, No Drawings

ALLATOSTATINS WHICH INHIBIT INSECT JUVENILE HORMONE BIOSYNTHESIS

This invention was made with government support under NIH grant DK-34549 awarded by the National Institute of Health. The government has certain rights in the invention.

BACKGROUND

This invention relates to novel allatostatins which have the potential for regulating the growth of certain insects and may in turn be useful in the area of insect control. Various means of insect control have been achieved over the years, including the use of arsenicals, oils, botanicals, DDT, carbamates and organophosphates. But these insecticides can be highly toxic to vertebrates, in addition to the target insects. Today, a more environmentally acceptable means of insect control is in great demand. Due to the growing awareness of health and ecological considerations, society is increasingly demanding the development of insect-specific control measures that are nonpollutant, safe, and compatible with integrated pest management systems. With increasing appreciation of the physiology and ecology of target and nontarget species, the demand for environmentally acceptable means of insect control can be met.

Insect neuropeptides are involved in the control of a wide range of physiological, biochemical and developmental functions, including water balance, lipid and carbohydrate metabolism, muscle contraction, reproduction, and growth and development. Several neurohormones that regulate homeostasis, metabolism and behavior have been characterized (J. J. Menn and A. B. Borkovec, *J. Agric. Food Chem.* 37,271 (1989)). In addition, four allatostatic neuropeptides that inhibit juvenile hormone synthesis have been isolated from brains of the virgin female coackroach *Diploptera punctata* (A. P. Woodhead et al. *Proc. Natl. Acad. Sci. USA* 86:5997 (1989) and G. E. Pratt et al. *BBRC* 163:1243 (1989)). This invention discloses new insect allatostatins which have functionally different N-termini.

One insect control strategy is the interference of insect juvenile hormone (JH) synthesis. Maintenance of a particular level of JH in the hemolymph, or change of JH titer as a signal for physiological changes in the insect, both require that the insect must be able to control the overall balance of JH synthesis, JH uptake and release by tissues, and JH clearance by degradation and excretion. In addition, the insect must be able to control the hemolymph volume. Control of JH synthesis is achieved by regulating the endocrine activity of the corpora allata (CA), the identified source of juvenile hormone (R. Feyereisen, in *Comprehensive Insect Physiology, Biochemistry and Pharmacology*, G. A. Kerkut and L. I. Gilbert, Eds. (Pergamon, Oxford, 1985) Vol. 7, pp. 391-429).

Neuropeptides (also referred to as neurohormones) which regulate the synthesis of JH are generally classified as allatotropins or allatostatins (J. J. Menn and A. B. Borkovec, *J. Agric. Food Chem.* 37:271 (1989)). The allatotropins are stimulatory substances and the allatostatins are inhibitory substances (R. Ruegg et al., *Experientia* 39:132 (1983) Woodhead et al and Pratt et al.) The allatostatins of this invention are inhibitory substances which inhibit juvenile hormone synthesis by the corpora allata. By inhibiting the synthesis of juvenile hormones, the normal development, maturation and reproduction of insects can be controlled.

SUMMARY OF THE INVENTION

This invention comprises novel allatostatins having the following sequence:

XVYNFGL-NH$_2$, in which X is LR, LP, RLP, AYSYVSEYKRLP, acetyl-AYSYV SEYKRLP or acetyl-RLP.

Illustrative allatostatins of the invention are:
AYSYVSEYKRLPVYNFGL-NH$_2$,
acetyl-AYSYVSEYKRLPVYNFGL-NH$_2$,
acetyl-RLPVYNFGL-NH$_2$,
RLPVYNFGL-NH$_2$,
LPVYNFGL-NH$_2$, and
LRVYNFGL-NH$_2$.

The peptides (allatostatins) of the invention inhibit juvenile hormone III synthesis by corpora allata (CA) in the cockroach *Diploptera punctata*. The target in the biosynthetic pathway is located prior to the conversion of farnesol to juvenile hormone III (JH).

All peptide sequences set out herein are written according to the convention in which the N-terminal amino acid (amino terminus, NH$_2$) is on the left and the C-terminal amino acid (carboxy terminus, COOH) is on the right. Unless indicated otherwise, all amino acids are L-amino acids. The N-terminal acetylated

group is designated "acetyl". The C-terminal amidated group is designated by (NH$_2$). The following terminology for amino acids (*J. of Biol. Chem.* 260:14 (1983)) is used herein:

| Amino Acid | Three-letter Code | One-letter Symbol |
|---|---|---|
| Alanine | Ala | A |
| Proline | Pro | P |
| Serine | Ser | S |
| Glycine | Gly | G |
| Glutamine | Gln | Q |
| Arginine | Arg | R |
| Leucine | Leu | L |
| Tyrosine | Tyr | Y |
| Phenylalanine | Phe | F |
| Valine | Val | V |
| Glutamic Acid | Glu | E |
| Lysine | Lys | K |
| Asparagine | Asn | N |

The invention provides sufficient quantities of natural allatostatin to permit sequence identification which in turn permits synthesis of large quantities of the natural allatostatin and the preparation of derivatives. From the disclosed sequence, genes encoding the protein can be constructed and put into vectors, which vectors may in turn be used to transform cells to express the peptide. Bacteria, yeast, mammalian, Baculovirus, plant and insect cells are suitable hosts for expressing the peptides.

The regulation of JH synthesis and release by the retrocerebral corpora allata is crucial to normal larval development, maturation and reproductive activities of insects. F. Engelmann, *Physiology of Insect Reproduction* (Pergamon, Oxford, 1970); L. I. Gilbert, *The Juvenile Hormones* (Plenum, New York, 1976). Environmental and physiological cues are integrated by the brain which in turn controls the corpora allata by stimulatory or inhibitory factors via nervous connections and indirectly via the hemolymph circulation. R. Feyereisen, in *Comprehensive Insect Physiology, Biochemistry and Pharmacology*, G. A. Kerkut and L. I. Gilbert, Eds. (Pergamon, Oxford, 1985) Vol. 7, pp. 391–429.

Until now the ability to study and understand insect allatostatins has been impeded due to the difficulty of obtaining allatostatins. The isolation of insect allatostatins is extremely difficult for two main reasons. First, allatostatins are present in insects in very small quantities that are measured in femtomoles (fmole) ($1 \times 10^{-15}$ mol). Secondly, allatostatins are highly labile to one or more of the conditions and substances used in the isolation process (e.g., temperature and solvents). In addition, the richest source of allatostatins, the neuroendocrine, organs, are usually microscopic so that thousands of insects have to be used in the initial extraction.

To begin the initial extraction, brain-complexes (cerebrum plus corpus cardiacum and corpora allata) from adult female *Diploptera punctata* are dissected, homogenized and centrifuged to yield a supernatant with stable activity. The supernatant is diluted with acetonitrile and applied to a liquid chromotograph for preliminary characterization. These fractions containing allatostatic activity are then further purified to remove any contaminating peptides. The procedure yields a pure allatostatin.

Using a combination of automated Edman degradation, tryptic digestion and tandem mass spectroscopy (MS/MS) sequence analysis of the isolated allatostatin reveals that it consists of eighteen amino acids, in the following sequence:

AYSYVSEYKRLPVYNFGL or
AYSYVSEYKRLPVYNFGI.

Fast action bombardment-mass spectroscopy (FAB-MS) determination of the molecular ion weight confirms the structure and establishes the fact that the native peptide is amidated. The carboxy terminal amidated (NH$_2$) form of the allatostatin with leucine (L) at the C-terminus of this sequence is synthesized, purified and found to have identical chromatographic patterns as the allatostatin recovered from insects. The synthetic allatostatin is biologically active in the in vitro assay described below.

The inhibition of JH synthesis and release by corpora allata is measured by an in vitro radiochemical assay which shows the test glands (corpora allata) to have maximum sensitivity to the action of the allatostatins of the invention. This assay for inhibition of JH synthesis is conducted as described by G. E. Pratt and J. R. Finney, in *Crop Protection Agents: their biological evaluation*, N. R. McFarlane, Ed. (Academic Press, New York, 1976)) except it is modified by the use of rapid partition instead of thin layer chromatography to isolate the newly synthesized JH and also modified by a reduction of incubation time to two hours.

The allatostatin of the invention inhibits JH biosynthesis of *Diploptera punctata* and is expected to inhibit that of other orders of insects which produce JH III. Examples of such orders of insects include Orthoptera, Dictyoptera, Diptera, Coleoptera and Hemiptera. Derivatives of the allatostatin also exhibit inhibition of the JHIII biosynthesis.

There exists a variety of means for using the allatostatins of the invention to inhibit JH III synthesis. The technology to synthesize small genes and to insert them into suitable vectors and express synthetic or natural genes in yeast or bacteria is now conventional. The microorganisms act as factories to produce peptides and can also serve as an encapsulation agent to help protect and distribute the biologically active ingredient. Examples of such approaches include the use of *Bacillus thuringiensis*, a commercial insecticide. Likewise, the insertion and expression of an insect allatostatin in plants is foreseen. In addition, Baculovirus, which have proven to be highly efficient cloning and expression vectors for foreign genes could carry allatostatin genes into target insects, and during replication, the transformed virus may produce and release large quantities of the hormones from within infected cells of the insects' bodies. Some potential attributes that allow inhibitors or their analogs to be effective for insect control include being stable, peptidomimetic and lipophilic enough to penetrate the cuticle and exert their action in vivo. If an inhibitor is lipophilic it can be effective when sprayed directly on insects or onto surfaces for contact action.

DESCRIPTION OF THE PREFERRED EMBODIMENTS

The following examples illustrate specific embodiments of the invention described herein.

EXAMPLE 1

Brain-complexes from adult females (*Diploptera punctata*) are dissected in Hank's salt solution, (GIBCO, Madison, Wis.) and stored in batches of 100–3,000 in 0.2M HCl 75% ethanol at −20° C. Homogenization (Thomas) and low temperature centrifugation (Sorval RC5B with an SA-600 angle head rotor spinning at 10000 rpm) yield a supernatant whose activity is stable. The supernatant is diluted to 10% acetonitrile and 0.1% trifluoroacetic acid (TFA) and loaded (at up to 400 brain equivalents) onto a $C_{18}$ Sep-Pak (Waters, Milford, Mass.). All bioactivity is recovered in a range of 18–35% acetonitrile in 0.1% TFA. This range is used as a standard preparation for preliminary characterization, as a procedure for removing non-volatile solutes from samples for bioassay, and as a starting point for further purification.

EXAMPLE 2

The $C_{18}$ Sep-Pak preparations from two batches of approximately 6,000 brain-complexes are purified as described below. Batches of crude allatostatin are first cleared of TFA by elution from a $C_{18}$ Sep-Pak in a range of 15–30% acetonitrile in 0.2% formic acid, then expanded with a solution of 0.2% formic acid, 1 mM dithiothreitol in acetonitrile to 95% acetonitrile and loaded onto a DIOL Sep-Pak; the chosen bioactivity elutes as the second of two bioactive peaks in a bracket of 10–40% $H_2O$ in acetonitrile and 0.1% TFA. This fraction is collected in a volume of 18 mL/1000 brain equivalents in siliconized vessels preloaded with 1–5 μg of purified carrier peptide (HPLC-purified oxidized insulin B chain (Sigma, St. Louis, Miss.) is used as protective carrier until final RP18 HPLC).

The allatostatin (AYSYVSEYKRLPVYNFGL-NH$_2$) is then purified on an RP4 reversed-phase cartridge. The post DIOL Sep-Pak samples are combined and expanded to 60 mLs with 0.1% TFA for recovery on a single $C_{18}$ Sep-Pak. After elution with 35% acetonitrile and addition of 1 μg of carrier peptide, the sample is filtered to 0.2 μm, expanded to 7.5 mL with 1% formic acid/0.3% triethylamine (pH 6.5) and loaded slowly (300 psi) onto a 75×4.1 mm RP4 HPLC column (Pierce) using a ⅛" ID Teflon sample loop. The column is eluted with a linear gradient of from 10–30% acetonitrile at 1 mL/min and 1.0% acetonitrile/min with isocratic modifiers (1% formic acid, 0.3% triethylamine). Monitoring is done at 276 nm with a Perkin-Elmer LC95 UV monitor (Perkin-Elmer, Norwalk, Conn.) employing a 4.5 μl flow cell. 0.5 mL fractions are collected into siliconized tubes preloaded with 1 μg of carrier peptide. The allatostatin (AYSYVSEYKRL-PVYNFGL-NH$_2$) eluted as a single peak of bioactivity at approximately 24.5% acetonitrile and represents aproximately 60% of the total bioactivity in the sample.

The allatostatin activity is finally purified on an RP18 column to separate it from contaminating peptides. A strong asymmetry of the UV peak is observed. Subsequent chromatography of synthetic material confirmed that asymmetric elution is a property of this compound in this system.

Primary sequence is determined using a combination of conventional Edman degradation chemistry along with several mass spectrometric techniques. After loading aliquots on a Model 470A gas-phase protein sequencer (Applied Biosystem, Inc., Foster City, Calif.) and obtaining partial sequence information, additional aliquots of the native peptide were used to determine a molecular weight value for the intact peptide by fast atom bombardment (FAB) ionization of sample suspended in a thioglycerol-HCl (2TGHCl) matrix. Analysis on a ZAB-SE instrument (VG Analytical Instruments, Manchester, England) indicated a distinct M+H ion at m/z 2169. This analysis was confirmed and a partial sequence determination was then obtained following collision activated dissociation (CAD) on two different instruments, a TSQ-70 (Finnigan Instruments) and a custom built FTMS system (Fourier Transformed Mass Spectrometer). Complete sequence information was finally obtained using HPLC-purified tryptic digestion fragments analyzed by MS/MS on the TSQ70 instrument. Failure of the C-terminus to methylate confirmed that the carboxy-terminus was amidated but the mass spectrometric data failed to elucidate whether the ultimate residue was leucine or isoleucine. Structural analogy to the already characterized allatostatins suggested that the peptide ended with leucinamide as the C-terminal residue. Substantiation of the leucinamide assignment (rather than isoleucinamide) is suggested by subsequent comparison of the activity data for the native compound versus synthetic, using the in vitro assay for JHIII biosynthesis. Additionally, the experimentally determined M+H of 2169 is consistent with a peptide of this composition (theoretical value 2169.4) allowing for amidation of the carboxy terminal residue.

EXAMPLE 3

The α-amidated compound is synthesized on an Applied Biosystems Model 430A Synthesizer in substantial accordance with the teaching of Example 6 and found to have the identical chromatographic patterns as the natural product. The RP18 cartridge column (115×2.1 mm, Pierce) is eluted with a 0.2 mL/min gradient of 0.1% TFA with increasing 0.08% TFA in 75% acetonitrile, generated by a Hewlett-Packard #1090 pump and monitored with a diode-array detector (Hewlett-Packard).

EXAMPLE 4

Biological activities are determined for all RP18•HPLC fractions. The synthetic peptide is biologically active. Juvenile hormone III is synthesized de novo from acetyl-CoA through the classical isoprenoid pathway to farnesyl pyrophosphate (D. A. Schooley and F. C. Baker, in *Comprehensive Insect Physiology, Biochemistry and Pharmacology*, G. A. Kerkut and L. I. Gilbert, Eds. (Pergamon, Oxford, 1985) Vol. 7, pp. 363–389) and the enzymatic conversion of farnesol to JH can be stimulated in vitro by exogenous 2E,6E farnesol (Aldrich, Milwaukee, Wis.) which presumably alleviates a limitation in the biosynthetic flux (R. Feyereisen, J. Koener, S. S. Tobe, in *Juvenile Hormone Biochemistry*, G. E. Pratt and G. T. Brooks, Eds. (Elsevier, Amsterdam, 1981), pp. 81–92). Dose-response assays reveal that this allatostatin is totally ineffective in the presence of 200 μM farnesol. The target of this allatostatin is therefore located early in the biosynthetic pathway. Juvenile hormone synthesis is determined at the end of two hours in these assays and bioactivity is measured as the ability of the peptide to inhibit biosynthesis of the JHIII. The peptide yields as determined from sequence analysis correspond to approximately 35 fmole/brain-complex. This is approximately one third the yield of the smaller known allatostatins (see G. E. Pratt et al. *Biochem. & Biophys. Res. Commun.* 163:1243 (1989) and A. P. Woodhead et al. *Prod. Natl. Acad. Sci.* 86:5997 (1989).

EXAMPLE 5

The inhibition of JH III synthesis and release by corpora allata (CA) from ten day old pregnant females is measured by an in vitro radiochemical assay. The three hour assay for inhibitors of JH synthesis (G. E. Pratt and J. R. Finney, in *Crop Protection Agents: their biological evaluation*, N. R. McFarlane, Ed. (Academic Press, New York, 1976) pp. 113–132) is modified by the use of rapid partition instead of thin layer chromatography to isolate the newly synthesized JH III (R. Feyereisen and S. S. Tobe, *Anal. Biochem.* 111: 372 (1981)) and modified by a reduction of incubation time to two hours. In each assay, run in seven replicates, one pair of CA was incubated with 50 μM (methyl-$^3$H) methionine and putative inhibitor in 0.1 mL of TC199 containing 2% Ficoll, 0.1% bovine serum albumin and 0.03% bacitracin. The test glands show maximum sensitivity to the allatostatic action of brain extracts. R. Feyereisen and D. E. Farnsworth, *Insect Biochem.* 17,939 (1987); S. M. Rankin and B. Stay, *J. Insec. Physiol.* 33, 551 (1987). Table 1 lists the synthesized sequences and their corresponding bioactivity.

TABLE 1

| Sequence | Bioactivity* as I.C.$_{50}$ (Day 10 Donors) |
|---|---|
| AYSYVSEYKRLPVYNFGL-NH$_2$ | 0.3 nM |
| acetyl-AYSYVSEYKRLPVYNFGL-NH$_2$ | 1.5 nM |
| acetyl-RLPVYNFGL-NH$_2$ | 30 nM |
| RLPVYNFGL-NH$_2$ | 270 nM |
| LPVYNFGL-NH$_2$ | 50 nM |
| LRVYNFGL-NH$_2$ | 118 nM |

*Bioactivity based on the inhibition of juvenile hormone synthesis and release measured by two hour in vitro radiochemical assay.

EXAMPLE 6

Peptides (allatostatins) are synthesized on an Applied Biosystem 430A synthesizer (Applied Biosystems, Foster City, Calif.) using symmetrical amino acid anhydrides as amino acid donors at each cycle (Kent, S.B.H. (1980) Biomedical Polymer, polymeric materials, and pharmaceuticals for biomedical use, 213–237, Academic Press, New York). For peptides with the C-terminal carboxy amide form, p-Methylbenzyhydrylamine resin (Applied Biosystems) is used as solid support. After HF cleavage from the solid support, the crude peptides are extracted with 33% acetic acid and lyophilized. The peptides are dissolved in 0.05% TFA and purified by reversed-phase C18 liquid chromatograpy. The structure and purity of the peptides are verified by amino acid analysis, FAB/MS and analytical HPLC.

For the amino terminal acetylated peptide, the peptide and p-Methylbenzhydrylamine resin is acetylated with a mixture of acetic anhydride and pyridine (1/1, V/V) for one hour before HF cleavage. As would be apparent to skilled artisans, various changes and modifications are possible and are contemplated within the scope of the invention described.

What is claimed is:

1. A synthetic allatostatin selected from the group consisting of:
   Ala-Tyr-Ser-Tyr-Val-Ser-Glu-Tyr-Lys-Arg-Leu-Pro-Val-Tyr-Asn-Phe-Gly-Leu-NH$_2$,
   acetyl-Ala-Tyr-Ser-Tyr-Val-Ser-Glu-Tyr-Lys-Arg-Leu-Pro-Val-Tyr-Asn-Phe-Gly-Leu-NH$_2$,
   acetyl-Arg-Leu-Pro-Val-Tyr-Asn-Phe-Gly-Leu-NH$_2$,
   Arg-Leu-Pro-Val-Tyr-Asn-Phe-Gly-Leu-NH$_2$,
   Leu-Pro-Val-Tyr-Asn-Phe-Gly-Leu-NH$_2$, and
   Leu-Arg-Val-Tyr-Asn-Phe-Gly-Leu-NH$_2$.

2. The allatostatin of claim 1 of the formula Ala-Tyr-Ser-Tyr-Val-Ser-Glu-Tyr-Lys-Arg-Leu-Pro-Val-Tyr-Asn-Phe-Gly-Leu-NH$_2$.

3. The allatostatin of claim 1 of the formula acetyl-Ala-Tyr-Ser-Tyr-Val-Ser-Glu-Tyr-Lys-Arg-Leu-Pro-Val-Tyr-Asn-Phe-Gly-Leu-NH$_2$.

4. The allatostatin of claim 1 of the formula acetyl-Arg-Leu-Pro-Val-Tyr-Asn-Phe-Gly-Leu-NH$_2$.

5. The allatostatin of claim 1 of the formula Arg-Leu-Pro-Val-Tyr-Asn-Phe-Gly-Leu-NH$_2$.

6. The allatostatin of claim 1 of the formula Leu-Pro-Val-Tyr-Asn-Phe-Gly-Leu-NH$_2$.

7. The allatostatin of claim 1 of the formula Leu-Arg-Val-Tyr-Asn-Phe-Gly-Leu-NH$_2$.

* * * * *